United States Patent
Chang

(10) Patent No.: US 8,156,935 B2
(45) Date of Patent: Apr. 17, 2012

(54) RESPIRATORY TUBE ASSEMBLY

(75) Inventor: Eric Chang, Taichung Hsien (TW)

(73) Assignee: Hsiner Co., Ltd., Taichung Hsien (TW)

( * ) Notice: Subject to any disclaimer, the term of this patent is extended or adjusted under 35 U.S.C. 154(b) by 614 days.

(21) Appl. No.: 12/418,693

(22) Filed: Apr. 6, 2009

(65) Prior Publication Data

US 2010/0252035 A1    Oct. 7, 2010

(51) Int. Cl.
  *A62B 9/04*   (2006.01)
  *A62B 7/10*   (2006.01)
  *A62B 19/00*  (2006.01)
  *A62B 23/02*  (2006.01)

(52) U.S. Cl. .......... 128/202.27; 128/205.12; 128/205.27

(58) Field of Classification Search .......... 128/202.27, 128/205.12, 205.27
See application file for complete search history.

(56) References Cited

U.S. PATENT DOCUMENTS

| | | | |
|---|---|---|---|
| 4,249,527 A * | 2/1981 | Ko et al. ............... | 128/204.18 |
| 4,456,008 A * | 6/1984 | Clawson et al. ........ | 128/205.19 |
| 4,457,305 A * | 7/1984 | Shanks et al. .......... | 128/205.12 |
| 6,439,231 B1 * | 8/2002 | Fukunaga et al. ....... | 128/207.14 |
| 2010/0122702 A1 * | 5/2010 | Reinboth et al. ........ | 128/205.27 |
| 2010/0258129 A1 * | 10/2010 | Huschke et al. ........ | 128/205.27 |

FOREIGN PATENT DOCUMENTS

| | | |
|---|---|---|
| DE | 3218771 | 5/1981 |
| DE | 3742888 A1 * | 7/1989 |
| GB | 1456570 | 11/1976 |

* cited by examiner

*Primary Examiner* — Loan Thanh
*Assistant Examiner* — Kathryn D Sheikh
(74) *Attorney, Agent, or Firm* — Occhiuti Rohlicek & Tsao LLP

(57) ABSTRACT

A respiratory tube assembly includes a three-way connector having first to third connecting sections, a container defining a receiving chamber and having a container surrounding wall and a projection projecting into the receiving chamber, a cover connected to the third connecting section and including a tubular recess, a recess bottom wall having a water-discharge opening, and an outer surrounding wall engaged detachably to the container surrounding wall, a valve head disposed movably within the tubular recess, and a valve rod extending into the receiving chamber. The valve head abuts against the third connecting section when the valve rod abuts against the projection so that the tubular recess communicates fluidly with the receiving chamber through the water-discharge opening. An inner tubular unit extends through the first and second connecting sections.

3 Claims, 5 Drawing Sheets

RESPIRATORY TUBE ASSEMBLY

BACKGROUND OF THE INVENTION

1. Field of the Invention

This invention relates to a respiratory tube assembly.

2. Description of the Related Art

Referring to FIG. 1, a conventional respiratory tube assembly includes an outer tube 1, an inner tube 2 disposed in the outer tube 1, a first connector 3 connected to one end of each of the inner and outer tubes 1, 2, a second connector 4 connected to the other end of each of the inner and outer tubes 1, 2 and connected to a patient end, and an air-discharge tube 5 connected to the first connector 3. The first connector 3 has an air supply portion 301 connected to a ventilator (not shown), and an air outlet portion 302 connected to the air-discharge tube 5. The ventilator supplies air having a predetermined temperature and humidity to the patient through the first connector 3, the inner tube 2, and the second connector 4. Air containing carbon dioxide exhaled by a patient is discharged through the second connector 4, the outer tube 1, the first connector 3, and the air-discharge tube 5.

Since the air exhaled by the patient to the outer tube 1 has a high moisture content and a high temperature, steam is usually condensed on an inner wall of the outer tube 1. This causes water to accumulate inside the outer tube 1. Thus, after using the conventional respiratory tube assembly for some time, the outer tube 1 must be disassembled from the respiratory tube assembly to remove the accumulated condensed water therein. Hence, use of the conventional respiratory tube assembly is inconvenient.

SUMMARY OF THE INVENTION

Therefore, the object of the present invention is to provide a respiratory tube assembly that is convenient to use.

According to this invention, a respiratory tube assembly comprises outer and inner tubular units. The outer tubular unit includes a three-way connector, first and second tubular sleeves, and a water-collecting device. The three-way connector has a main tubular section, first and second connecting sections extending outwardly and respectively from two opposite ends of the main tubular section and extending in two opposite directions along an axis of the main tubular section, and a third connecting section extending from the main tubular section between the first and second connecting sections along a direction transverse to the axis. Each of the first, second, and third connecting sections has a diameter smaller than that of the main tubular section. The first tubular sleeve has a first end portion sleeved on the first connecting section, and a second end portion opposite to the first end portion. The second tubular sleeve has a third end portion sleeved on the second connecting section, and a fourth end portion opposite to the third end portion. The water-collecting device includes a container, and a cover covering the container and connected to the third connecting section. The container is connected detachably to the cover, and has a container bottom wall, a container surrounding wall extending upwardly from and cooperating with the container bottom wall to define a receiving chamber, and a projection projecting from the container bottom wall into the receiving chamber. The cover includes a top wall that is recessed downwardly to form a tubular recess, a recess surrounding wall surrounding the tubular recess, a recess bottom wall connected to the recess surrounding wall oppositely of the top wall, and an outer surrounding wall extending downwardly from an outer end periphery of the top wall, surrounding the recess surrounding wall, and engaged detachably to the container surrounding wall. The recess bottom wall extends into the receiving chamber, and has a water-discharge opening. The water-collecting device further includes a valve member that has a valve head disposed movably within the tubular recess, and a valve rod extending downwardly from the valve head into the receiving chamber through the water-discharge opening to abut against the projection. The valve head is spaced apart from the recess bottom wall, and abuts against the third connecting section when the valve rod abuts against the projection so that the tubular recess communicates fluidly with the receiving chamber through the water-discharge opening. The inner tubular unit extends from the first tubular sleeve into the second tubular sleeve through the first and second connecting sections and the first main tubular section of the first three-way connector, and has a fifth end portion proximate to the second end portion, and a sixth end portion proximate to the fourth end portion.

BRIEF DESCRIPTION OF THE DRAWINGS

Other features and advantages of the present invention will become apparent in the following detailed description of the preferred embodiment of the invention, with reference to the accompanying drawings, in which.

DETAILED DESCRIPTION OF THE PREFERRED EMBODIMENT

Figure 1:
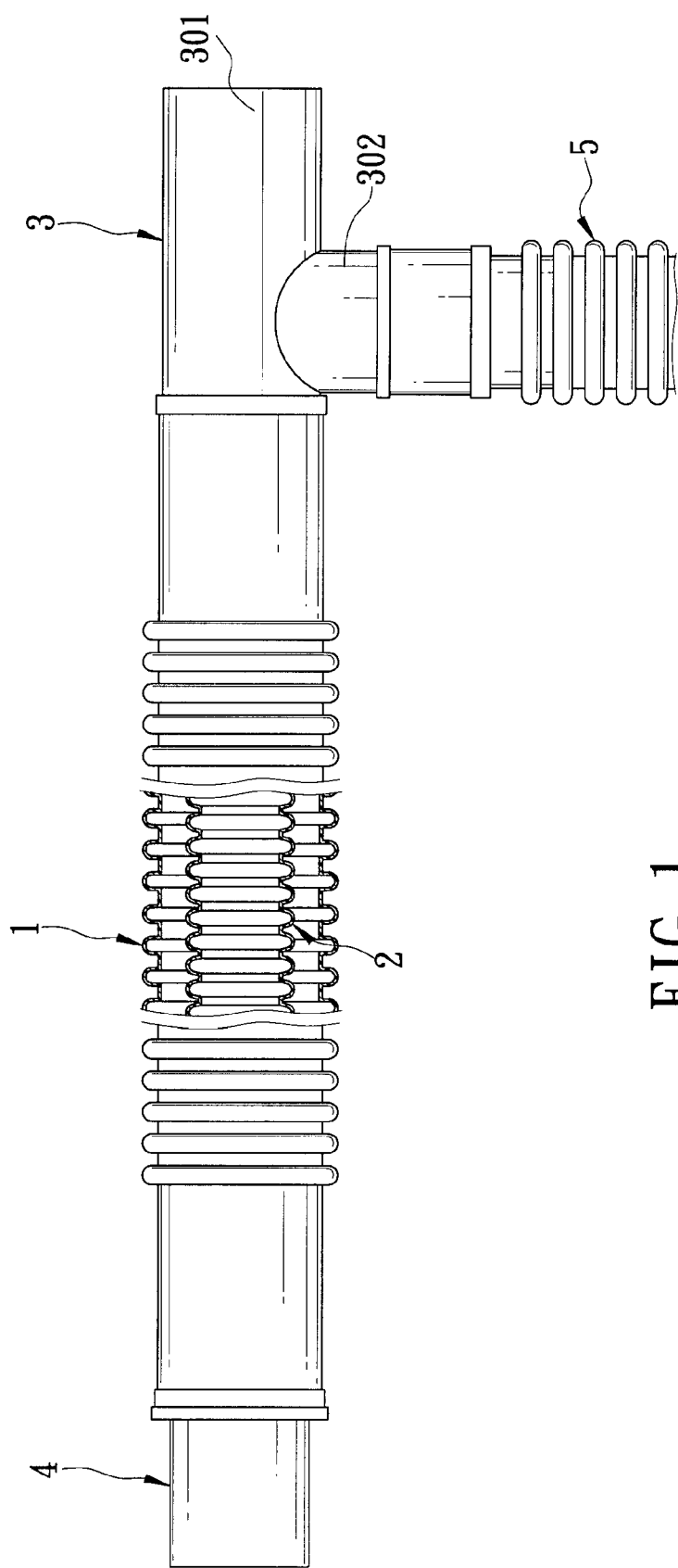
FIG. 1 is a fragmentary partly sectional view of a conventional respiratory tube assembly.
Figure 2:
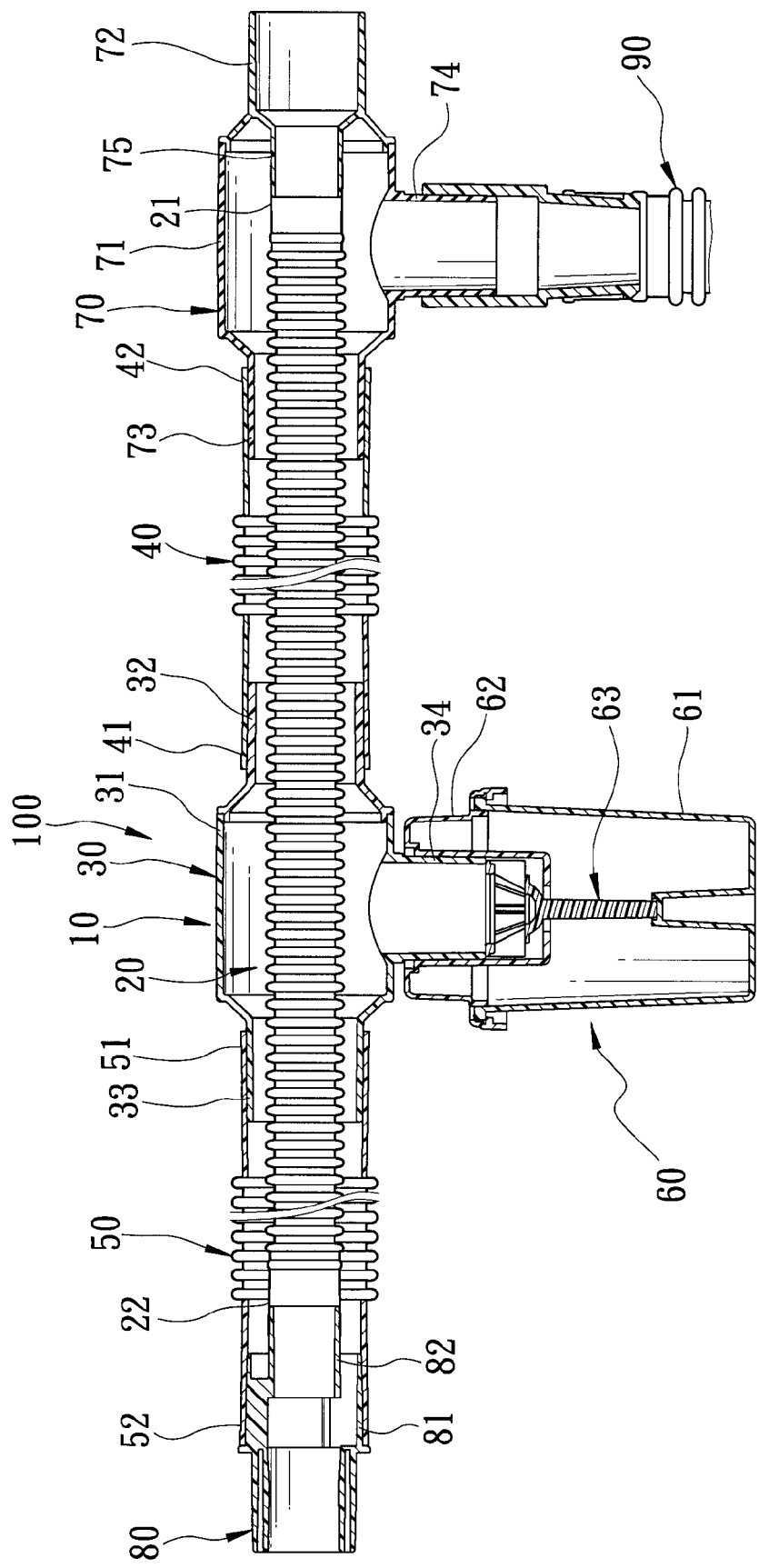
FIG. 2 is a fragmentary sectional view of a respiratory tube assembly according to the preferred embodiment of this invention.

Referring to FIGS. 2 to 5, a respiratory tube assembly 100 according to the preferred embodiment of the present invention is shown to comprise an outer tubular unit 10 and an inner tubular unit 20.

The outer tubular unit 10 includes a first three-way connector 30, a first tubular sleeve 40, a second tubular sleeve 50, a water-collecting device 60, a second three-way connector 70, a coupling element 80, and an air-discharge tube 90.

The first three-way connector 30 has a first main tubular section 31, first and second connecting sections 32, 33 extending outwardly and respectively from two opposite ends of the first main tubular section 31 and extending in two opposite directions along an axis of the first main tubular section 31, and a third connecting section 34 extending from the first main tubular section 31 between the first and second connecting sections 32, 33 along a direction transverse to the axis. Each of the first, second, and third connecting sections 32, 33, 34 has a diameter smaller than that of the first main tubular section 31.

The first tubular sleeve 40 has a first end portion 41 connected to the first connecting section 32, and a second end portion 42 opposite to the first end portion 41.

The second tubular sleeve 50 has a third end portion 51 connected to the second connecting section 33, and a fourth end portion 52 opposite to the third end portion 51.

The water-collecting device 60 includes a container 61 and a cover 62. The container 61 is connected detachably to the cover 62, and has a container bottom wall 611, a container surrounding wall 612 extending upwardly from and cooperating with the container bottom wall 611 to define a receiving chamber 613, a projection 614 projecting from the container bottom wall 611 into the receiving chamber 613, and a plurality of spaced-apart engaging pieces 615 provided on a top outer face of the container surrounding wall 612.

The cover 62 covers the container 61, and includes a top wall 621 that is recessed downwardly to form a tubular recess 624, a recess surrounding wall 622 extending downwardly from the top wall 621 and surrounding the tubular recess 624, a recess bottom wall 623 connected to the recess surrounding wall 622 oppositely of the top wall 621, an outer surrounding wall 626 extending downwardly from an outer end of the top wall 621 and surrounding the recess surrounding wall 622, and a plurality of spaced-apart engaging grooves 627 provided on an inner face of the outer surrounding wall 626. The recess bottom wall 623 has a water-discharge opening 625 communicated with the tubular recess 624. The cover 62 is connected to the third connecting section 34 by inserting the third connecting section 34 fittingly into the tubular recess 624.

A valve member 63 is provided in the tubular recess 624, and has a valve head 631 disposed movably within the tubular recess 624, and a valve rod 632 extending downwardly from the valve head 631 through the water-discharge opening 625. The third connecting section 34 is spaced apart from the valve head 631 when the container 61 and the cover 62 are not interconnected.

To interconnect the container 61 and the cover 62, the container 61 is rotated relative to the cover 62 until the engaging pieces 615 of the container surrounding wall 612 engage respectively the engaging grooves 627 of the outer surrounding wall 626. The recess surrounding wall 622 extends into the receiving chamber 613 at this time, and abuts against the projection 614. Further, the valve head 631 is spaced apart from the recess bottom wall 623, and abuts against the third connecting section 34, so that the tubular recess 624 communicates fluidly with the chamber 613 through the water-discharge opening 625.

The second three-way connector 70 has a second main tubular section 71 aligned axially with the first main tubular section 31, first and second connecting sections 72, 73 extending outwardly and respectively from two opposite ends of the second main tubular section 71 and extending in two opposite directions along an axis of the second main tubular section 71, a third connecting section 74 extending from the second main tubular section 71 between the first and second connecting sections 72, 73 along a direction transverse to an axis of the second main tubular section 71, and an inner tube 75 connected to the first connecting section 72 and extending into the second main tubular section 71. The second end portion 42 is connected to the second connecting section 73. In this embodiment, the first connecting section 72 of the second three-way connector 70 may be connected to a ventilator (not shown), and the dimensions of the second three-way connector 70 are similar to those of the first three-way connector 30.

The coupling element 80 has an outer tube 81 connected to the fourth end portion 52, and an inner tube 82 disposed co-axially in the outer tube 81. In this embodiment, the coupling element 80 is connected to a patient end.

The air-discharge tube 90 is connected to the third connecting section 74 of the second three-way connector 70.

The inner tubular unit 20 extends from the first tubular sleeve 40 into the second tubular sleeve 50 through the first and second connecting sections 32, 33 and the first main tubular section 31, and has a fifth end portion 21 proximate to the second end portion 42, and a sixth end portion 22 proximate to the fourth end portion 52 and connected to the inner tube 82. The fifth end portion 21 extends into the second main tubular section 71, and connects to the inner tube 75.

Through the aforementioned connections, the ventilator (not shown) supplies air having a predetermined temperature and humidity to a patient by passing the air through the first connecting section 72, the inner tube 75, the inner tubular unit 20, and the coupling element 80. Air containing carbon dioxide exhaled by the patient passes through the coupling element 80, the second tubular sleeve 50, the first three-way connector 30, the first tubular sleeve 40, and the second three-way connector 70, and discharges through the air-discharge tube 90.

Figure 3:
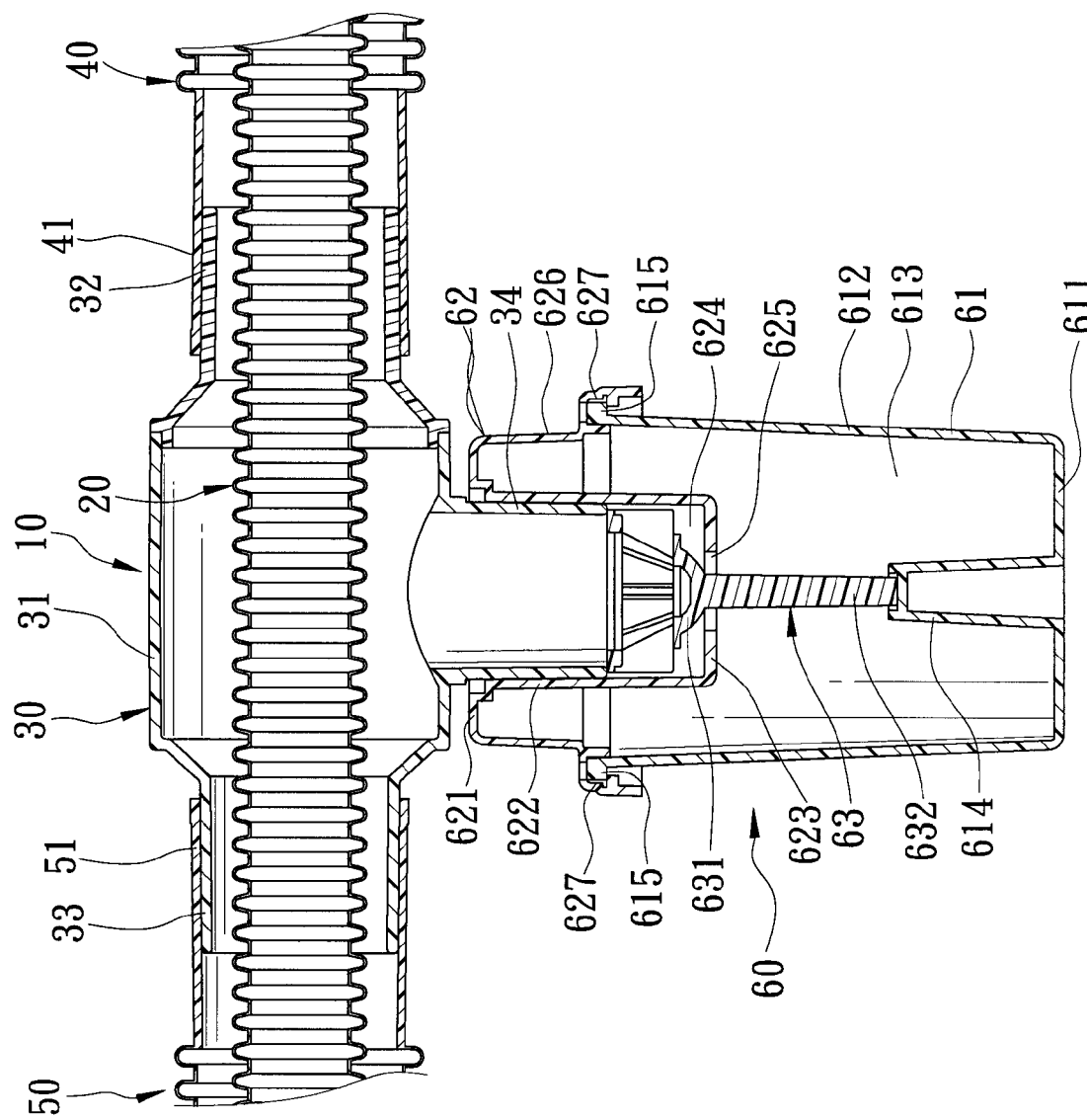
FIG. 3 is an enlarged sectional view of a portion of FIG. 2.
Figure 4:
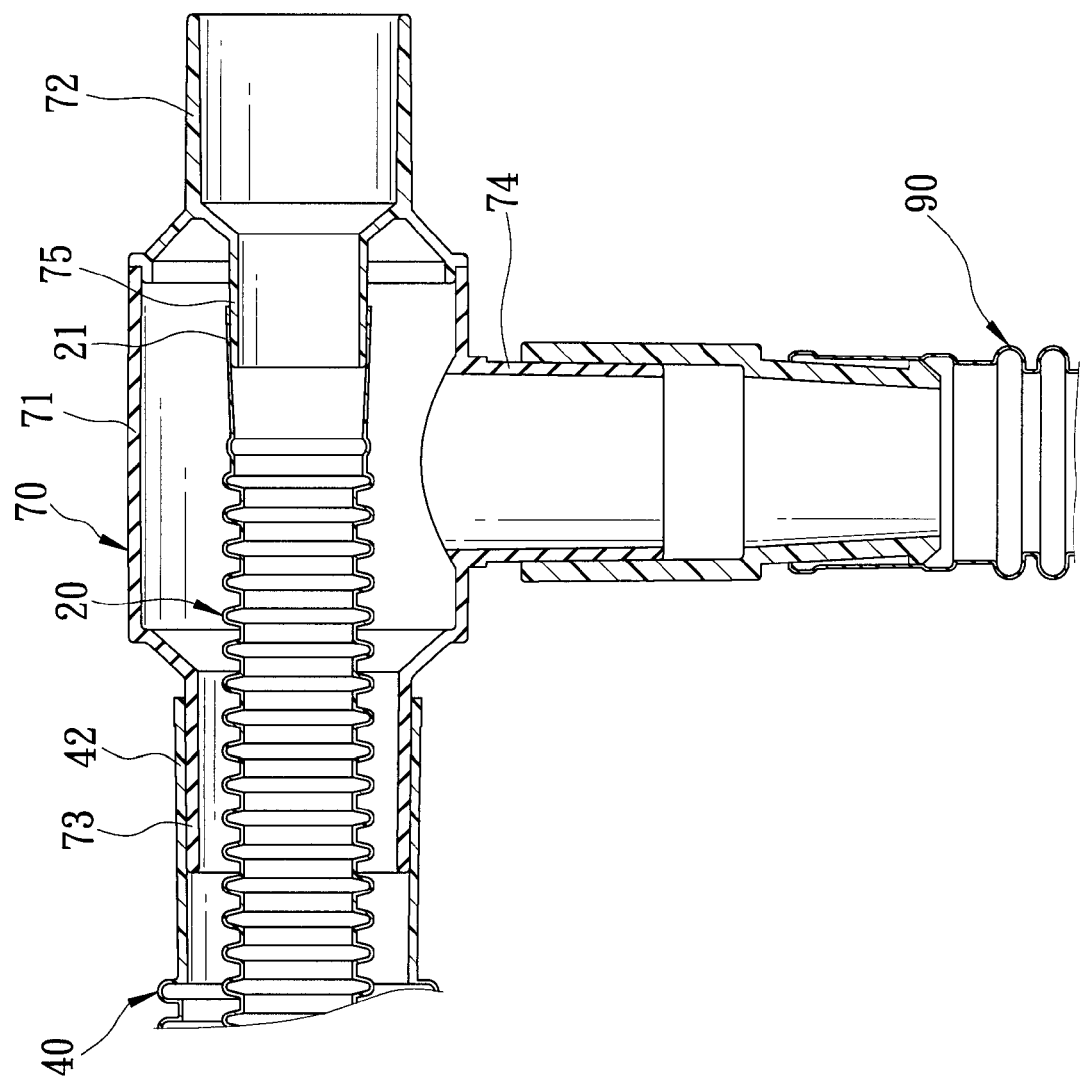
FIG. 4 is an enlarged sectional view of another portion of FIG. 2.
Figure 5:
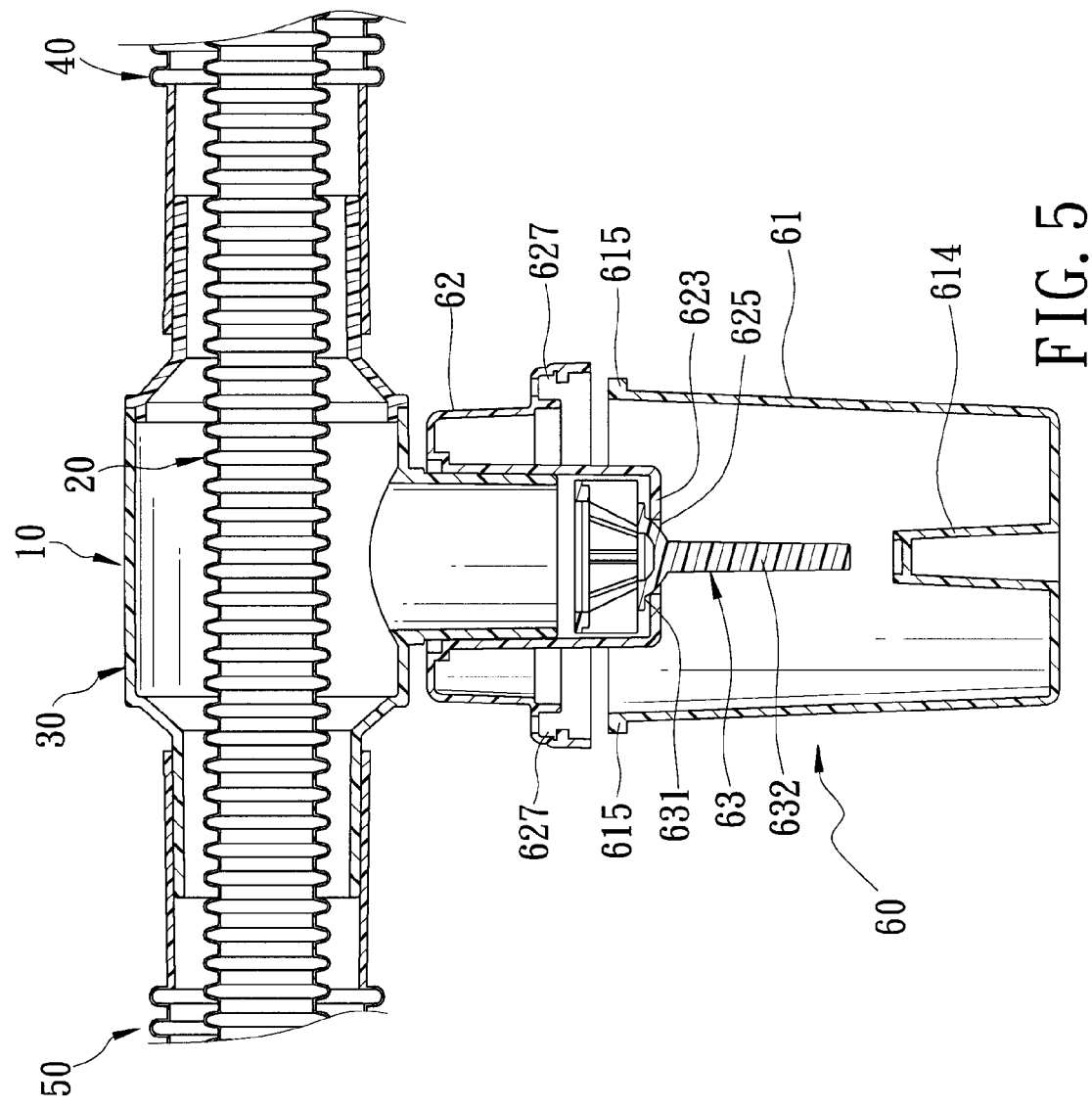
FIG. 5 is a view similar to FIG. 3, but illustrating a container in a state detached from a cover.

Further, with reference to FIG. 3, when there is condensation buildup in the first and second tubular sleeves 40, 50, water condensed therein can flow into the container 61 through the first three-way connector 30. When the amount of water in the container 61 reaches a predetermined height, with reference to FIG. 5, a medical professional rotates the container 61 relative to the cover 62 so as to move the engaging pieces 615 away from the engaging grooves 627, so that the container 61 can be detached from the cover 62, and the water in the container 61 can be discarded. When the container 61 is detached from the cover 62, since the projection 614 is moved away from the valve rod 632 so that the valve rod 632 does not abut against the projection 614, the valve head 631 falls onto the recess bottom wall 623 by gravity, and seals the water-discharge opening 625.

The advantages of the present invention may be summarized as follows:

1. The outer tubular unit 10 is provided with the water-collecting device 60 so as to collect condensed water buildup in the first and second tubular sleeves 40, 50. The medical professional simply detaches the container 61 from the cover 62 to discard the water in the container 61.

2. Since the dimensions of the first and second three-way connectors 30, 70 are exactly the same, a similar die can be used to manufacture the first and second three-way connectors 30, 70, so that the manufacturing cost of the present invention can be reduced to a minimum.

While the present invention has been described in connection with what is considered the most practical and preferred embodiment, it is understood that this invention is not limited to the disclosed embodiment but is intended to cover various arrangements included within the spirit and scope of the broadest interpretations and equivalent arrangements.

I claim:

1. A respiratory tube assembly comprising:
    an outer tubular unit and an inner tubular unit, said outer tubular unit including a first three-way connector, a first tubular sleeve, a second tubular sleeve, and a water-collecting device;
    said first three-way connector having a first main tubular section, first and second connecting sections extending outwardly and respectively from two opposite ends of said first main tubular section and extending in two opposite directions along an axis of said first main tubular section, and a third connecting section extending from said first main tubular section between said first and second connecting sections along a direction transverse to said axis, each of said first, second, and third connecting sections having a diameter smaller than that of said first main tubular section;
    said first tubular sleeve having a first end portion sleeved on said first connecting section, and a second end portion opposite to said first end portion;

said second tubular sleeve having a third end portion sleeved on said second connecting section, and a fourth end portion opposite to said third end portion;

said water-collecting device including a container, and a cover covering said container and connected to said third connecting section, said container being connected detachably to said cover and having a container bottom wall, a container surrounding wall extending upwardly from and cooperating with said container bottom wall to define a receiving chamber, and a projection projecting from said container bottom wall into said receiving chamber, said cover including a top wall that is recessed downwardly to form a tubular recess, a recess surrounding wall surrounding said tubular recess, a recess bottom wall connected to said recess surrounding wall oppositely of said top wall, and an outer surrounding wall extending downwardly from an outer end periphery of said top wall, surrounding said recess surrounding wall, and engaged detachably to said container surrounding wall, said recess bottom wall extending into said receiving chamber and having a water-discharge opening;

said water-collecting device further including a valve member that has a valve head disposed movably within said tubular recess, and a valve rod extending downwardly from said valve head into said receiving chamber through said water-discharge opening to abut against said projection, said valve head being spaced apart from said recess bottom wall and abutting against said third connecting section when said valve rod abuts against said projection so that said tubular recess communicates fluidly with said receiving chamber through said water-discharge opening;

said inner tubular unit extending from said first tubular sleeve into said second tubular sleeve through said first and second connecting sections and said first main tubular section of said first three-way connector, and having a fifth end portion proximate to said second end portion, and a sixth end portion proximate to said fourth end portion.

2. The respiratory tube assembly of claim 1, wherein said outer tubular unit further includes an air-discharge tube, and a second three-way connector having a second main tubular section aligned axially with said first main tubular section, first and second connecting sections extending outwardly and respectively from two opposite ends of said second main tubular section and extending in two opposite directions along an axis of said second main tubular section, a third connecting section extending from said second main tubular section between said first and second connecting sections of said second three-way connector along a direction transverse to said axis of said second main tubular section and connected to said air-discharge tube, and an inner tube connected to said first connecting section of said second three-way connector and extending into said second main tubular section, said second end portion being connected to said second connecting section of said second three-way connector, said fifth end portion extending into said second main tubular section and connecting said inner tube of said second three-way connector.

3. The respiratory tube assembly of claim 1, wherein said outer tubular unit further includes a coupling element having an outer tube connected to said fourth end portion, and an inner tube disposed coaxially in said outer tube and connected to said sixth end portion.

* * * * *